United States Patent [19]

Cue, Jr. et al.

[11] 4,412,958

[45] Nov. 1, 1983

[54] STEREOSPECIFIC SYNTHESIS OF 5-PHENYL-2S-PENTANOL

[75] Inventors: Berkeley W. Cue, Jr., Gales Ferry; Bernard S. Moore, Waterford, both of Conn.

[73] Assignee: Pfizer Inc., New York, N.Y.

[21] Appl. No.: 404,075

[22] Filed: Aug. 5, 1982

Related U.S. Application Data

[63] Continuation-in-part of Ser. No. 312,012, Oct. 16, 1981, abandoned.

[51] Int. Cl.³ .................. C07C 137/00; C07C 29/132; C07C 49/213
[52] U.S. Cl. .................................. 260/456 R; 560/53; 560/61; 568/331; 568/663; 568/814
[58] Field of Search .................. 568/814, 663, 331; 560/61, 53; 260/456 R

[56] References Cited

PUBLICATIONS

Temnikov et al., Chem. Abs., vol. 73 (1970) 14104f.
Mislow et al., Jour. Amer. Chem. Soc., vol. 84 (1962) 1940-1944.

Primary Examiner—Bernard Helfin
Attorney, Agent, or Firm—Charles J. Knuth; Albert E. Frost; Robert K. Blackwood

[57] ABSTRACT

5-Phenyl-2S-pentanol is synthesized stereospecifically from S ethyl lactate. The method provides easily purified 5-phenyl-2S-pentanol useful in the synthesis of central nervous system active (CNS) agents such as levonantradol.

17 Claims, No Drawings

STEREOSPECIFIC SYNTHESIS OF 5-PHENYL-2S-PENTANOL

CROSS REFERENCE TO RELATED APPLICATION

This application is a continuation-in-part of copending application Ser. No. 312,012, filed Oct. 16, 1981 and now abandoned.

BACKGROUND OF THE INVENTION

The present invention meets a need for a stereospecific synthesis of 5-phenyl-2S-pentanol from readily available optically pure starting material (S-ethyl lactate) which at the same time provides product readily purified and free of contaminating alcohols such as phenethyl alcohol or 3-phenylpropyl alcohol. Such contaminating alcohols are extremely difficult to remove; if not removed, these contaminants generally render the 5-phenyl-2S-pentanol unacceptable in the synthesis of CNS active agents such as levonantradol

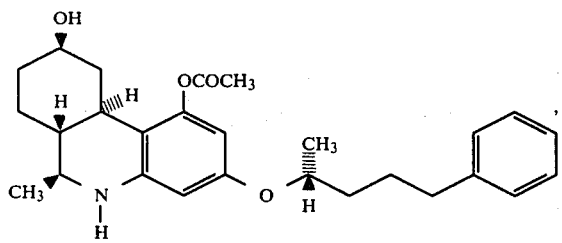

(Johnson, U.S. Pat. No. 4,260,764; Johnson et al., J. Clin. Pharmacol. 21, pp. 271S–282S, 1981; Milne and Johnson, ibid., pp. 367S–374S), since the contaminating alcohol carries through the synthesis of the levonantradol yielding a corresponding contaminant in the CNS agent, e.g., a compound having 2-phenylethoxy sidechain in place of the 5-phenyl-2-pentyloxy sidechain.

Levonantradol, derived from the present 5-phenyl-2S-pentanol, has found clinical use in man as an analgesic agent, Jain et al., ibid., pp. 320S–326S; and and as an antiemetic agent in cancer chemotherapy, Laszlo et al., ibid., pp. 48S–53S; Penta et al., ibid., pp. 11S–22S; Cronin et al., ibid., pp. 43S–50S; see also Johnson and Milne, U.S. Pat. No. 4,228,169.

The best stereospecific synthesis of 5-phenyl-2S-pentanol previously available employed the reaction of phenethyl magnesium halide with S-propylene oxide; it has been virtually impossible to form 5-phenyl-2S-pentanol free of phenethyl alcohol by this process, particularly on a large scale as required for commercial preparation of CNS agents such as levonantradol.

Certain intermediates employed in the present synthesis are known compounds, viz., methyl 2S-benzyloxypropionate, of the formula (VI) below, and 2S-benzyloxy-1-propanol of the formula (V) below. These compounds have been described by Mislow et al., J. Am. Chem. Soc., 84, pp. 1940–1944 (1962), the latter in deuterated forms. The first named compound was derived from S-ethyl lactate by reaction with benzyl bromide in alcohol in the presence of gross quantities of silver oxide, an extremely expensive reagent, a process to be contrasted with the present process which completely avoids this reagent. Reduction of methyl 2S-benzyloxypropionate with lithium aluminum deuteride by Mislow et al. gave 2S-benzyloxy-1-propanol-1-$d_2$; the latter was converted to 2S-benzyloxy-1-propanol-1-$d_3$ via its p-bromobenzenesulfonate ester, cf. compounds of the formula (IV) below.

SUMMARY OF THE INVENTION

The present invention is concerned with an advantageous process for the stereospecific synthesis of the chiral alcohol, 5-phenyl-2S-pentanol, of the formula

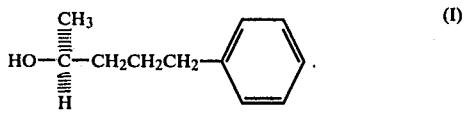
(I)

The final processing stage comprises hydrogenation over a noble metal catalyst of a chiral ketone of the formula

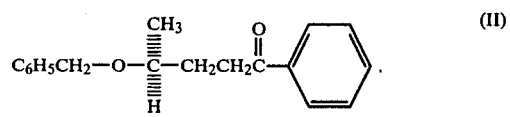
(II)

The chiral ketone of the formula (II) is in turn derived by hydrolysis and decarboxylation of a chiral ester of the formula

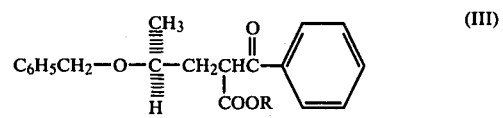
(III)

wherein R is $(C_1-C_4)$alkyl.

The chiral benzyl ether-esters of the formula (III) are prepared by reaction of an alkali metal salt of a $(C_1-C_4)$alkyl benzoylacetate, e.g.,

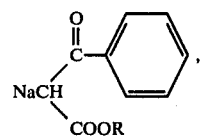

with a compound of the formula

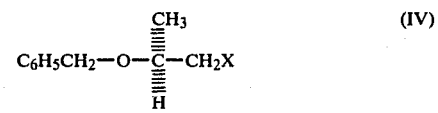
(IV)

wherein X is I, Br, Cl, $OSO_2CH_3$ or

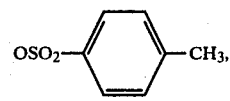

optionally in the presence of iodide ion. The preferred value of X is I. The halides of the formula (IV) wherein X is Cl, Br or I are derived by the reaction of an alkali metal halide with a sulfonate ester of the formula (IV) wherein X is $OSO_2CH_3$ or

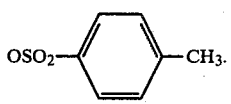

The preferred sulfonate ester is the mesylate ester.

The mesylate or tosylate of the formula (IV) wherein X is OSO₂CH₃ or

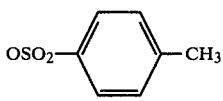

are derived by reaction of methanesulfonyl or p-toluenesulfonyl chloride with 2S-benzyloxy-1-propanol, a chiral compound of the formula

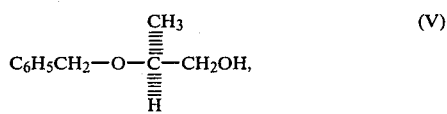

(V)

in turn derived by the hydride reduction of a benzylated lactate ester of the formula

(VI)

wherein R is $(C_1-C_4)$alkyl, as previously described by Mislow et al.

Alternatively, halides of the formula (IV) wherein X is Cl, Br or I are formed by reaction of the alcohol (V) with halide forming reagents such as $SOCl_2$, $PBr_3$ or $PI_3$.

The benzylated lactate ester of the formula (VI) can be prepared from the corresponding lactate ester of the formula

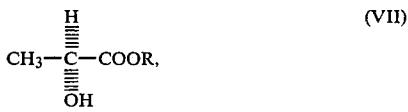

(VII)

wherein R is $(C_1-C_4)$alkyl, also according to Mislow et al., whereby S-methyl lactate is reacted with benzyl bromide in ethyl ether in the presence of a gross amount of silver oxide. When an inexpensive base, such as sodium hydroxide, is used as catalyst in place of silver oxide, the reaction is accompanied by extensive or complete racemization. Surprisingly, by reacting benzyl mesylate with an excess of lactate ester as solvent (about three molar equivalents total is preferred), with no catalyst present and simple heating to about 110°–140° C. (preferably 120°–130° C.), the desired chiral benzyl ether of the formula (VI) is formed in high yield. No significant racemization is observed in this novel process.

The present invention also encompasses intermediate, chiral compounds of the formulae (II), (III) and (IV).

5-Phenyl-2S-pentanol is employed in the synthesis of CNS agents (such as levonantradol) as set forth in U.S. Pat. Nos. 4,206,225; 4,232,018; 4,235,913; 4,243,674; 4,260,764; 4,263,438; 4,270,005; and 4,283,569. The same patents set forth methods for using said CNS agents.

DETAILED DESCRIPTION OF THE INVENTION

The various process steps of the present invention are readily carried out, using readily available and relatively inexpensive starting materials and reagents.

In order to convert the chiral ketone of the formula (II) to 5-phenyl-2S-pentanol, the former (neat or preferably dissolved or suspended in a reaction inert solvent medium) is contacted with hydrogen in the presence of a noble metal catalyst at an appropriate temperature and pressure until reduction of the carbonyl group to methylene and hydrogenolysis of the benzyl group (if present) is complete. The desired 5-phenyl-2S-pentanol is recovered by conventional procedures. This will generally involve simple recovery of the catalyst by filtration, using a suitable solvent for transfer and wash, and removal of solvent from the combined filtrate and wash by evaporation. If desired, the product is further purified by distillation at reduced pressures; however, this step is usually unnecessary, one salient feature of the present invention being that simple isolation/purification procedures yield 5-phenyl-2S-pentanol free of contaminating alcohols and thus suitable for the synthesis of levonantradol and other CNS active agents.

As used herein "reaction inert solvent medium" refers to any media which is a solvent or suitable suspending agent for reactant(s), reagent(s) or product(s), which does not react in a manner with said reactant(s), reagent(s) or product(s) to significantly reduce the yield of the desired product.

If the present hydrogenation is carried out in the presence of a solvent or solvents, lower boiling solvents are preferred, since they are readily removed from the product by evaporation, obviating any possible need for distillation of the product. Suitable solvents include $(C_1-C_4)$alkanols, ethers (such as diethyl ether, diisopropyl ether, tetrahydrofuran, dioxane, 1,2-dimethoxyethane), hydrocarbons (such as toluene) or halogenated aliphatic hydrocarbons (such as ethylene chloride). It is preferred that a protic solvent (e.g., water or a $(C_1-C_4)$alkanol) be present in at least a minor portion. It is also preferred that a minor portion of a strong acid (e.g., hydrochloric acid) be present, since such conditions promote hydrogenolysis of the benzyl group, as well as hydrogenation of intermediate alcohols of the formula

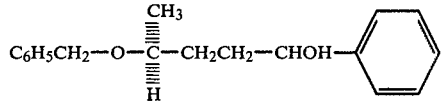

The same solvents optionally used in the hydrogenation are suitable for transfer and recovery of the catalyst.

The temperature and pressure of the hydrogenation is not critical; a wide range of temperature (e.g., 0°–75° C.) and pressure (e.g., subatmospheric up to 100 atmospheres or more) being suitable, depending in part on the catalyst system employed. It is generally preferred to operate at low pressures (e.g., 1–7 atmospheres), since less sophisticated equipment is required for the hydrogenation reaction. Ambient temperatures (e.g., 15°–25° C.) are generally preferred, although lower catalyst levels required at higher temperatures will in some cases dictate a preference for higher temperatures on simple economic grounds. It will be further understood that with less active catalysts, pressures higher in the range (i.e., greater than 7 atmospheres) and temperatures greater than 25° C. will be necessary in order to achieve reasonable reaction rates.

The noble metal catalysts as employed in the present invention include platinum, palladium, rhenium, rhodium and ruthenium, either of the supported or nonsupported type, as well as the known catalytic compounds thereof such as the oxides, chlorides, etc. Examples of suitable catalyst supports include carbon, silica and barium sulfate. The catalysts are preformed or formed in situ by prereduction of an appropriate salt of the catalytic compound. The latter is accomplished simply by suspending the catalyst precursor in the hydrogenation medium and hydrogenating it prior to adding the substrate and continuing the hydrogenation. Alternatively, all of the components can be incorporated at once and hydrogenation commenced. The former procedure has the advantage of permitting the operator to separately determine the quantity of hydrogen absorbed during the catalyst prereduction and substrate hydrogenation phases. The preferred noble metal catalyst for the present hydrogenation is palladium, preferably of the supported type. The preferred support is carbon. The level of palladium on the support is not critical, although it is usually in the range of 5-10% by weight, more or less. For ease in handling, it is preferred that the catalyst preparation be "water-wet", generally containing an amount of water about equal to the weight of noble metal and support, e.g., "50% water-wet". The preferred catalyst system readily functions at the preferred lower pressures and temperatures, particularly when the preferred portion of protic solvent and a small amount of strong acid are present.

The chiral ketone of the formula (II) is prepared by hydrolysis and decarboxylation of the corresponding ester of the formula (III). Either base or acid is used as catalysts for the hydrolysis and decarboxylations; base catalysis is preferred, using a polar, preferably protic, solvent such as water, a ($C_1$-$C_4$)lower alkanol or mixture thereof. An alkali metal hydroxide is the preferred basic catalyst; most preferred is potassium hydroxide. The temperature is generally elevated, e.g., 60°-100° C., sufficiently high to attain a reasonable rate of reaction without undue degradation of reactants or products. A preferred solvent system is about 50:50 by volume of water:ethanol, with the reaction conveniently carried out under reflux, about 79°-80° C. Under the recommended conditions, it is preferred to continue the reaction until both hydrolysis and decarboxylation are complete, i.e., the intermediate acid of the formula

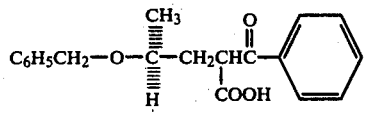

is generally not isolated.

The ester of the formula (III) is prepared by nucleophilic displacement of the group X (Cl, Br, I, $OSO_2CH_3$,

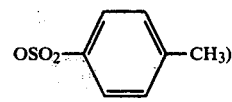

in a compound of the formula (IV) with the anion of a ($C_1$-$C_4$)alkyl benzoylacetate (in the form of an alkali metal salt with a ($C_1$-$C_4$)-alkyl benzoylacetate, preferably the sodium salt). A wide variety of solvents are suitable for this reaction, including alcohols, acetonitrile, dimethylformamide, etc., the only requirement being that the solvent be inert towards reactants and product, and that the reactants have some degree of solubility. Preferably, the solvent should be less acidic than the benzoylacetate ester, so as to maintain a high concentration of the displacing anion. The temperature employed for this reaction is not critical (e.g., 0°-140° C.). It should be high enough to provide a reasonable rate, but not so high as to lead to undue decomposition. As is well known in the art, rate will vary with the nature of the value of X (e.g., I>Br>Cl), with the solvent, and, to a lesser degree, the value of R and which alkali metal salt is employed. The reaction time should be such that the reaction is nearly complete (e.g., >95% conversion when equivalent amounts of the compound (IV) and alkyl benzoylacetate salt are employed) to maximize yields (e.g., 1 hour to several days depending on temperature). These reactions are readily monitored by thin layer chromatography, employing one of a variety of commercially available silica gel plates containing an ultraviolet indicator. Suitable eluants are hexane-ethyl acetate mixtures, e.g., 6:1 hexane:ethyl acetate. As the reaction proceeds, an equivalent of strong base is neutralized. For this reason pH is also used as an aid in monitoring the reaction. Because the nucleophilic displacement occurs rapidly and cleanly, the preferred value of X is I. In this particular case dimethylformamide is well-suited as solvent with a reaction time of about 2 hours used at 120°-126° C. When X is other than I, it is preferred to catalyze the present reaction with iodide ion, in effect forming intermediate organic iodide in situ.

The chiral halides of the formula (IV) wherein X is Cl, Br or I are in turn prepared from a sulfonate ester of the formula (IV) wherein X is $OSO_2CH_3$ or

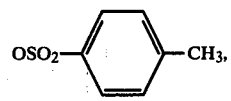

again a nucleophilic displacement reaction. The considerations of the preceding paragraph are therefore applicable to the present case. In the preparation of the preferred organic iodide from the preferred mesylate, the reaction of excess sodium iodide (1.5 to 2.5 equivalents) with the mesylate ester in acetone at reflux for about 20-24 hours represents a convenient set of conditions for attaining a high yield over this step.

The chiral sulfonate ester of the formula (IV), wherein X is $OSO_2CH_3$ or

is readily prepared under conditions standard for the sulfonation of alcohols, e.g., the reaction of substantially one equivalent of the appropriate organic sulfonyl chloride with the chiral alcohol of the formula (V) in the presence of at least one equivalent of a tertiary amine such as triethylamine, in an inert solvent medium at ambient or preferably reduced temperature (e.g., −10° to 5° C.). Preferred solvents are low boiling (e.g., methylene chloride) so as to be readily removed by evaporation.

The chiral alcohol of the formula (V) is prepared by the standard hydride reduction of an O-benzyllactate ester of the formula (VI) as detailed hereinafter in specific example 3, or by analogy to the lithium aluminum deuteride reduction of the chiral methyl O-benzyllactate as carried out by Mislow et al., as cited above. The present hydride reduction of esters of the formula (VI) can be carried out under mild conditions with a variety of hydride reducing agents, e.g., lithium aluminum hydride (per se or as a 50% suspension in oil), "Red-al" (a 70% solution of bis(2-methoxyethoxy)aluminum hydride in benzene), or sodium or lithium borohydride. When lithium aluminum hydride is the reagent, it is essential that the solvent be aprotic and free of reducible groups (carbonyl function of any type, nitrile, nitro, aliphatic halogen, sulfonate, etc.). The preferred solvents are ethers such as tetrahydrofuran, dioxane, 1,2-dimethoxyethane, bis(2-methoxyethyl)ether, etc. When Red-al is the reducing agent, aromatic hydrocarbons such as benzene or toluene are also well-suited as solvents. Sodium borohydride will generally require the use of a protic solvent such as ethanol.

The conversion of chiral ($C_1$–$C_4$)alkyl lactate of the formula (VII) to its O-benzyl derivative, without racemization and without use of expensive silver oxide as catalyst represents another salient feature of the present invention. Surprisingly, this reaction is accomplished by simple warming of benzyl mesylate in an excess of the chiral ($C_1$–$C_4$)alkyl lactate (e.g., about three equivalents, with heating at 80°–110° C. for 1–4 hours, depending upon the temperature used, representing particularly well-suited conditions). The excess lactate ester can be separated by distillation. However, it is preferable to carry this contaminant through the next step, whereby it is converted to highly water-soluble propylene glycol, readily removed by extraction from 2-benzyloxy-1-propanol (V).

The benzyl mesylate is prepared from benzyl alcohol and methanesulfonyl chloride according to methods detailed above.

The present invention is illustrated by the following examples. However, it should be understood that the invention is not limited to the specific details of these examples.

EXAMPLE 1

Benzyl Methanesulfonate

Under nitrogen methylene chloride (1.4 liter), benzyl alcohol (129.6 g, 1.2 moles) and triethylamine (182 g, 1.8 moles) were combined, stirred and cooled to −5° C. in an ice-water-acetone bath. A solution of methanesulfonyl chloride (150 g, 1.31 moles) in 100 ml of methylene chloride was added over 49 minutes, maintaining the temperature between −5° and 2° C. After stirring for 10 minutes at 0°-2° C., the reaction was diluted with 500 ml of water, precooled to 5° C. The organic layer was separated, washed 2×500 ml of cold water, dried over $MgSO_4$, filtered and evaporated in vacuo to yield title product as a light yellow oil [190 g; 85%; $^1$H-NMR ($CDCl_3$) delta (ppm): 2.9 (s, 3H), 5.2 (s, 2H), 7.4 (m, 5H); $R_f$ 0.75 ($CH_2Cl_2$)]. This product was refrigerated until used in the next step.

EXAMPLE 2

Ethyl 2S-Benzyloxypropionate

Under nitrogen, benzyl methanesulfonate (181.5 g, 0.975 mole) was combined and stirred with S ethyl lactate (ethyl 2S-hydroxypropionate; 393 g, 3.33 moles) and the resulting solution heated on a steam bath to 94° C. over 15 minutes and held for 1.5 hours at this temperature. The reaction mixture was cooled to 45° C. and poured into 2 liters of cold toluene. Water (500 ml) was added and the mixture stirred for 5 minutes. The aqueous phase was separated and extracted with 200 ml fresh toluene. The organic layers were combined, washed in sequence 2×500 ml $H_2O$, 1×500 ml saturated $NaHCO_3$, 2×500 ml water and 1×500 ml saturated NaCl, dried over $MgSO_4$, filtered, and evaporated in vacuo to yield crude product as an oil [228 g, 112%; $[alpha]_D^{25}$ −60.8°, C=1.11 ($CHCl_3$)], which $^1$H-NMR indicated to be contaminated with ethyl lactate. Distillation in vacuo gave, after an early boiling solvent fraction 1 [25 ml, b.p. to 79° C./1.2 mm; $[alpha]_d$ −6.9°, C=1.13 ($CHCl_3$)]; fractions 2–8 [74 ml, b.p. 82° C./1.3 mm to 114° C./3 mm; $[alpha]_D$ −42.1° to −76.2°, C=1.09–1.16 ($CHCl_3$)] as a mixture of S ethyl lactate and title product; and fractions 9–12 [57 ml; b.p. 115° C./3 mm, 98°–100°/0.75 mm, 102°–106° C./1.0 mm; $[alpha]_D$ −80.0° to −83.7°, C=1.01–1.17 ($CHCl_3$)] of substantially pure title product. A higher boiling pot residue of 49 g remained. A portion of fraction 10 (3 g) was voided of traces of ethyl lactate by taking up in 100 ml of hexane and equilibrating with 30 ml $H_2O$. The hexane layer was separated, washed 3×30 ml $H_2O$, dried over $MgSO_4$, filtered and concentrated to an oil [2.4 g; $R_f$ 0.32 (6:1 hexane:ethyl acetate); $[alpha]_D^{25}$ −83.3°, C=1.13 ($CHCl_3$)].

EXAMPLE 3

2S-Benzyloxy-1-propanol

Fractions 2–9 and 12 from the above distillation (106.1 g total weight, 0.45 moles of ethyl 2S-benzyloxypropionate and 0.25 moles of S ethyl lactate) was dissolved in 100 ml of anhydrous ethanol and the solution added dropwise to a stirred mixture of $NaBH_4$ (37.85 g, 1.0 mole) and 500 ml of anhydrous ethanol under nitrogen over a one hour period. The temperature was maintained at 25°–30° C. during addition by cooling with a 20° C. water bath. After stirring for 20 hours at ambient temperature, the reaction mixture was cooled to 10° C. and 95 ml of 12 N HCl (1.14 mole) added dropwise over 15 minutes under a sweep of nitrogen. The resulting slurry was filtered with 100 ml ethanol wash. The filtrate and wash were combined and concentrated in vacuo to 150 ml. The concentrate was diluted with 200 ml of water and 300 ml of ethyl acetate, the pH was adjusted from 1.5 to 9.0 with 50 ml of 4 N NaOH (causing precipitated solids to dissolve) and the layers were separated. The aqueous phase was washed 1×100 ml and then 1×50 ml of ethyl acetate. The three organic layers were combined, washed 2×150 ml H$_2$O and then 1×150 ml saturated NaCl, dried over MgSO$_4$, filtered, and evaporated to yield title product as an oil [50.5 g; [alpha]$_D^{25}$ +47.9, C=1.08 (CHCl$_3$); +27.736 (neat); R$_f$ 0.1 (CH$_2$Cl$_2$)].

EXAMPLE 4

2S-Benzyloxy-1-propyl Mesylate

Under nitrogen, 2S-benzyloxy-1-propanol (49.8 g, 0.3 mole), 400 ml of CH$_2$Cl$_2$ and triethylamine (40.5 g, 0.4 mole) were combined, stirred and cooled to −5° C. in an ice-water-acetone bath. Maintaining −5° C., methanesulfonyl chloride (37.8 g, 0.33 mole) in 30 ml CH$_2$Cl$_2$ was added over one hour. After stirring at −5° C. for 0.5 hour, H$_2$O (200 ml at 5° C.) was added. The layers were separated and the aqueous layer washed 1×100 ml CH$_2$Cl$_2$. The combined organic layers were washed in sequence 1×100 ml H$_2$O, 1×100 ml 1 N HCl, 1×100 ml H$_2$O, 1×100 ml saturated NaHCO$_3$ and 1×100 ml H$_2$O, dried over MgSO$_4$, filtered, and concentrated in vacuo to yield title product as an oil [72.2 g, 98.5%; [alpha]$_D^{25}$ +7.7, C=1.00 (CHCl$_3$); R$_f$ 0.6 (CH$_2$Cl$_2$)].

EXAMPLE 5

2S-Benzyloxy-1-propyl Iodide

Under nitrogen with stirring, sodium iodide (90 g, 0.6 mole) was dissolved in one liter dry acetone. At 32° C., 2S-benzyloxy-1-propyl mesylate (71.5 g, 0.293 mole) was added. The reaction mixture was warmed to 59°–60° C. (gentle reflux) and held for 20 hours, at which time tlc indicated about 20% starting material to remain. Additional sodium iodide (30 g, 0.2 mole) was added and refluxing continued for 3 hours. The reaction was cooled to room temperature and filtered with acetone wash. The combined filtrate and wash was concentrated to 150 ml of oily solids, diluted with 300 ml toluene and 200 ml H$_2$O, the layers separated and the aqueous phase extracted 2×100 ml toluene. The three organic layers were combined, washed 2×200 ml H$_2$O, dried over MgSO$_4$, filtered and evaporated to yield title product as an oil [79 g, 96%; [alpha]$_D$= +8.0°, C=1.08 (CHCl$_3$), $^1$H-NMR (CDCl$_3$) delta (ppm): 1.4 (d, 3H), 3–3.6 (m, 3H), 4.6 (s, 2H), 7.35 (s, 5H)].

EXAMPLE 6

Ethyl 2-Benzoyl-4S-benzyloxyvalerate

Under nitrogen, sodium hydride (50% in oil, 13.6 g, 0.283 mole) was washed with 3×200 ml of dry hexane. To the resulting hexane wet NaH, 130 ml dimethylformamide was added, followed by the dropwise addition of ethyl benzoylacetate (54.4 g, 0.283 mole) over 45 minutes, maintaining the temperature 28°–32° C. with a 10° C. water bath and sweeping away evolved H$_2$ with N$_2$. After stirring for 85 minutes at 25° C., 2S-benzyloxy-1-propyl iodide (78 g, 0.283 mole) was added with 40 ml of dimethylformamide for rinse. The reaction mixture was then heated and stirred at 122°–126° C. for 2 hours (during which solids precipitated), cooled to 70° C., diluted with 350 ml toluene and 560 ml of ice water, and the resulting layers separated. The aqueous layer was extracted 3×150 ml toluene. The four organic layers were combined, washed 3×150 ml H$_2$O and then 1×150 ml saturated NaCl, dried over MgSO$_4$, filtered and concentrated in vacuo to yield title product as an oil [90 g, 94%; [alpha]$_D^{25}$ +15.8°, C=1.12 (CHCl$_3$); R$_f$ 0.35 (6:1 hexane:ethyl acetate)].

EXAMPLE 7

4S-Benzyloxy-1-phenyl-1-pentanone

Ethyl 2-benzoyl-4S-benzyloxyvalerate (89 g, 0.26 mole), ethanol (175 ml), water (175 ml) and KOH (85%, 51 g, 0.8 mole) were combined with stirring under nitrogen, during which the temperature rose to 45° C. The reaction mixture was heated to 79° C. under a reflux condenser and held for 18 hours. The reaction mixture was cooled to 25° C., diluted with 350 ml of water and 300 ml of toluene, the layers separated, and the aqueous layer washed 1×200 ml and 2×150 ml toluene. The organic layers were combined, washed 2×200 ml H$_2$O and 1×200 ml saturated NaCl, dried over MgSO$_4$, filtered and concentrated in vacuo to yield title product as an oil [45.5 g, 65%; [alpha]$_D^{25}$ +21.92°, C=1.20 (CHCl$_3$); R$_f$ 0.55 (6:1 hexane:ethyl acetate)].

EXAMPLE 8

5-Phenyl-2S-pentanol

4S-Benzyloxy-1-phenyl-1-pentanone (45 g, 0.168 mole) in 150 ml of toluene, 15 ml of absolute alcohol and 3 drops concentrated HCl were hydrogenated over 4 g 50% water wet 5% Pd/C at 50–60 psig and 25° C. After hydrogenating for 6 hours, an additional 4 g catalyst was charged and hydrogenation continued for 2.5 hours, by which time three equivalents of hydrogen were consumed and there had been no uptake over the final 1.5 hour period. The catalyst was recovered by filtration. The filtrate was neutralized by stirring over a 5 cc volume of solid NaHCO$_3$, dried over MgSO$_4$, filtered and concentrated in vacuo to yield title product as an oil [22 g, 80%; [alpha]$_D^{25}$ +8.63, C=1.02 (CHCl$_3$); R$_f$ 0.2 (6:1 hexane:ethyl acetate)]. If desired the title product was further purified by simple distillation to remove traces of tlc origin material, b.p. 90–94/0.7 mm with nearly quantitative recovery.

We claim:

1. A process for preparing a 2S chiral alcohol of the formula

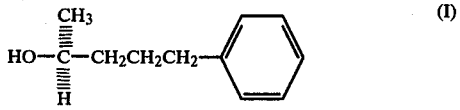

which comprises hydrogenation over a noble metal catalyst of a chiral ketone of the formula

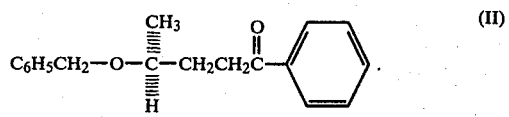

2. A process of claim 1 wherein the noble metal catalyst is palladium.

3. A process for the preparation of a 2S chiral alcohol of the formula

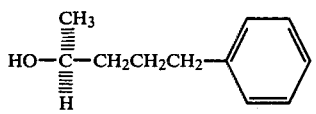  (I)

which comprises:
(a) hydrogenation over a noble metal catalyst of compound of the formula

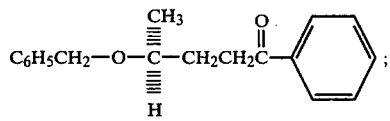  (II)

and
(b) preparation of the chiral ketone of the formula (II) by hydrolysis and decarboxylation of a chiral ester of the formula

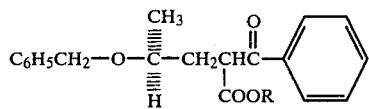  (III)

wherein R is $(C_1-C_4)$alkyl.

4. A process of claim 3 wherein R is ethyl.

5. A process for the preparation of a 2S chiral alcohol of the formula

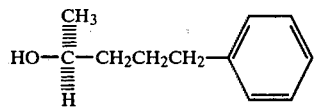  (I)

which comprises:
(a) hydrogenation over a noble metal catalyst of a chiral ketone of the formula

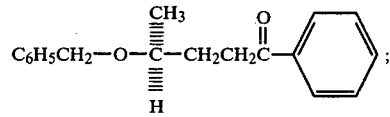  (II)

(b) preparation of the chiral ketone of the formula (II) by hydrolysis and decarboxylation of a chiral ester of the formula

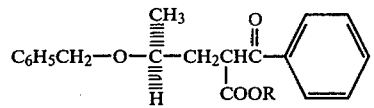  (III)

wherein R is $(C_1-C_4)$alkyl;
(c) preparation of the chiral ester of the formula (III) by reaction of an alkali metal salt of a $(C_1-C_4)$alkyl benzoylacetate with chiral compound of the formula

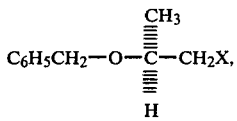  (IV)

wherein X is I, Br, Cl, $OSO_2CH_3$ or

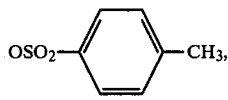

optionally in the presence of iodide ion;
(d) when X is I, Br or Cl, preparation of the chiral halide compound of the formula (IV) wherein X is I, Br or Cl by reaction of halide ion with a sulfonate ester compound of the formula (IV) wherein X is $OSO_2CH_3$ or

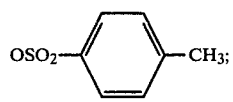

(e) formation of the sulfonate ester of the formula (IV) wherein X is $OSO_2CH_3$ or

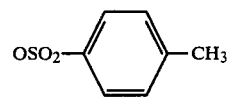

by reaction of methanesulfonyl chloride or p-toluene sulfonyl chloride with a chiral compound of the formula

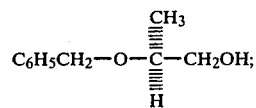  (V)

(f) formation of the chiral compound of the formula (V) by hydride reduction of a chiral ester of the formula

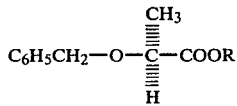  (VI)

wherein R is $(C_1-C_4)$alkyl; and
(g) preparation of the chiral ester of the formula (VI) by reaction of benzyl methanesulfonate neat with an excess of a chiral 2S lactate ester of the formula

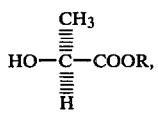  (VII)

wherein R is $(C_1-C_4)$alkyl.

6. A process of claim 5 wherein the chiral ester of the formula (III) is formed by reaction of the benzoylacetate salt with the iodide of the formula (IV) wherein X is I.

7. A process of claim 6 wherein the iodide of the formula (IV) wherein X is I is formed by reaction of sodium iodide with the mesylate ester of the formula (IV) wherein X is $OSO_2CH_3$.

8. The process of claim 7 wherein R is ethyl and the alkali metal salt of the benzoylacetate is sodium.

9. A process for the preparation of a chiral ester of the formula

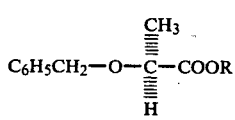

wherein R is $(C_1-C_4)$alkyl by reaction of benzyl methanesulfonate neat with an excess of a chiral 2S lactate ester of the formula

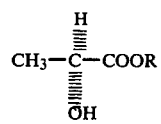

wherein R is $(C_1-C_4)$alkyl.

10. The process of claim 9 wherein R is ethyl.

11. A chiral ketone of the formula

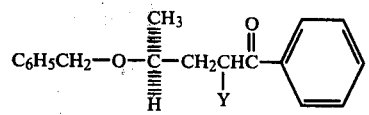

wherein Y is hydrogen or —COOR and R is $(C_1-C_4)$alkyl.

12. The chiral ketone of claim 11 wherein Y is hydrogen.

13. A chiral ketone of claim 11 wherein Y is —COOR.

14. The chiral ketone of claim 13 wherein R is ethyl.

15. A chiral compound of the formula

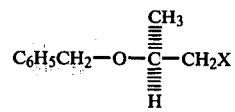

wherein X is I, Br, Cl or $OSO_2CH_3$.

16. The chiral compound of claim 15 wherein X is I.

17. The chiral compound of claim 15 wherein X is $OSO_2CH_3$.

* * * * *